United States Patent [19]
Eisenbarth et al.

[11] Patent Number: 4,745,197
[45] Date of Patent: May 17, 1988

[54] FLEXIBLE BISMALEIMIDES

[75] Inventors: Philipp Eisenbarth, Bad Durkheim; Anton Hesse, Weinheim; Jan Holoch, Heidelberg; Roland Peter, Ludwigshafen, all of Fed. Rep. of Germany

[73] Assignee: BASF Aktiengesellschaft, Ludwigshafen, Fed. Rep. of Germany

[21] Appl. No.: 68,070

[22] Filed: Jun. 30, 1987

[51] Int. Cl.⁴ ........................................... C07D 403/12
[52] U.S. Cl. ..................................... 548/521; 526/262
[58] Field of Search .......................................... 548/521

[56] References Cited

U.S. PATENT DOCUMENTS

| | | | |
|---|---|---|---|
| 2,850,351 | 9/1958 | Moore et al. | 548/521 X |
| 3,236,895 | 2/1966 | Lee et al. | 564/505 |
| 3,654,370 | 4/1972 | Yeakey | 564/480 |
| 3,855,239 | 12/1974 | Crivello | 548/521 X |
| 3,887,582 | 6/1975 | Halub et al. | 548/521 |
| 3,920,768 | 11/1975 | Kwiatkowski | 548/521 X |
| 3,966,531 | 6/1976 | Bargain | 548/521 X |

FOREIGN PATENT DOCUMENTS 0148534  7/1985  European Pat. Off. ............ 548/521

*Primary Examiner*—Joseph Paul Brust
*Attorney, Agent, or Firm*—William G. Conger

[57] ABSTRACT

Bismaleimides having the general formula

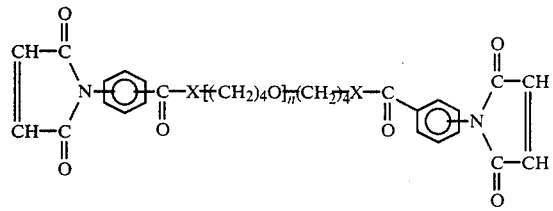

in which n is a whole number between 5 and 70 and —X— is —O— or —NH— are prepared through the reaction of the corresponding amino-terminated polyoxybutylenes with 2 moles of maleic anhydride. They are suited as toughening agents in high grade reactive resins.

5 Claims, No Drawings

FLEXIBLE BISMALEIMIDES

BACKGROUND OF THE INVENTION

1. Field of the Invention

The subject invention relates to flexible bismaleimides which are prepared through the reaction of maleic anhydride with an amino-terminated polyoxybutylene.

2. Description of the Related Art

Bismaleimide resins are heat curable reactive resins which are finding increasing applications in the aerospace, automotive, machine construction and electronic fields, for example, in the form of filled and unfilled molding compositions, as well as fiber reinforced prepregs. These thermosetting materials show good heat resistance and high modulus of elasticity, however they share a major disadvantage in their comparatively high degree of brittleness. This characteristic is thought to be caused by the high crosslinking density. When these materials are used as structural components in the aerospace industry, the fiber reinforced composite materials used are faced with severe requirements in terms of ductility and toughness, which cannot be satisfactorily fulfilled by presently available bismaleimide resins.

The use of rubber to toughen bismaleimide resins has not proven successful for a variety of reasons. A different concept resides in incorporation of flexible chain segments into the polymer network through the use of maleimide-group terminated polymers. However, up until now, such flexible bismaleimides have not possessed the range of properties necessary for their intended applications.

SUMMARY OF THE INVENTION

It has now been found that the use of maleimide monomers whose terminal maleimide rings are coupled to a movable linear molecular chain having a high molecular weight results in toughened bismaleimide resin systems having a desirable balance of physical properties. This is achieved according to the process of the subject invention by incorporating polyoxybutylene segments (polytetrahydrofuran) into the polymer chain of the bismaleimide.

DESCRIPTION OF THE PREFERRED EMBODIMENTS

The bismaleimides of the subject invention thus have the general structural formula:

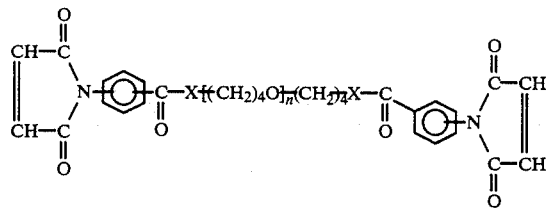

in which n is a whole number between 5 and 70 and —X— stands for —O— or —NH—.

These bismaleimides are prepared through the reaction of 2 moles of maleic anhydride with 1 mole of an amino-terminated polyoxybutylene having the formula:

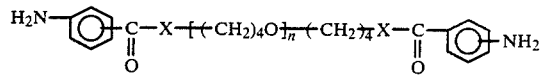

The preparation of polyoxybutylenes having aromatic amino terminal groups is described, for example, described in Japanese Patent JA 59/199 715 by transesterification of polyoxybutylene with amino benzoic esters (1 equivalent per OH group) during which process the lower molecular alcohol component is removed by distillation. Alternatively, a polyoxybutylene having aliphatic amino groups having the formula:

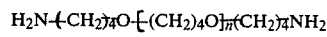

may be reacted with amino benzoic esters, whereby amino benzamide terminal groups form. Of course, it is possible to utilize polyoxybutylenes having both terminal amino and terminal hydroxyl groups. In this case, the product, after reacting with the aminobenzoic acid ester, would contain terminal aminophenyl groups linked to the polyoxybutylene chain by amide and ester linkages, respectively. The molecular weight of the polytetrahydrofuran used can vary over a wide range, between about 400 and about 5,000 Daltons; preferred is a range of from about 600 to about 2400 Daltons.

For the preparation of the corresponding bismaleimides from the amino-terminated polyoxybutylenes, any suitable process for preparing bismaleimides from diamines may be utilized.

For example, production of bismaleimides through conversion of the amino-terminated polyoxybutylenes may be effected by reaction with maleic anhydride in an aprotic, polar, organic solvent, for example acetone, methylethylketone, diethylketone, cyclohexanone, dimethylformamide, dimethylacetamide or N-methylpyrrolidone, at temperatures of from 0° to 30° C. Efficaciously, from 1 to 1.5 equivalents of maleic anhydride are used per amino group. The bisamidocarboxylic acid/intermediate which results does not need to be isolated, but may be directly converted into the bismaleimide with accompanying loss of the water. The dehydration of the bis-amidocarboxylic acid takes place in the presence of a lower molecular weight carboxylic anhydride, preferably acetic anhydride, at temperatures between 40° and 80° C. In addition, metal salts or tertiary amines may be added as cyclization catalysts. Especially active metal compounds are the nitrates, halides, acetates, acetylacetonates or alkoxides of lithium, sodium, magnesium, calcium, nickel, manganese and cobalt. Preferred are the corresponding transition metal salts. Triethylamine is especially preferred as a tertiary amine.

For isolating the product it is useful to completely distill off the solvent under vacuum using slight warming, and separate the oily residue from the acetic acid formed and from the catalyst by addition of water. For better phase separation during the washing procedure, which must be repeated several times in order to achieve a pH of about 7, it is advantageous to dilute the organic phase using a solvent which is imiscible with water, for example dichloromethane. After completing the washing procedure, the organic phase is dried and the solvent is removed in vacuuo. The product is obtained as a viscous, yellowish to brown oil. In the case where the product has a higher molecular weight, it may harden to become wax-like or it may crystallize. Identifying the product may be achieved using both IR and NMR spectroscopy, as well as by determination of the unsaturation, which, in general, is between 80 and 95 percent of the theoretical value. The solubility of the bismaleimide is very high in many organic solvents, for example acetone and dichloromethane.

The bismaleimides are particularly suitable as flexibilizers for bismaleimides resins, and may also be suitable for use in unsaturated polyester resins, vinyl ester resins, cyanate ester resins or as cross linkers for paints and adhesives. They cure to form transparent, highly-flexible molding compounds without the necessity of the purposeful addition of free radical catalysts.

EXAMPLE a) Preparation of a polyoxybutylene having aromatic amino terminal groups

A mixture containing 3000 grams of a polytetrahydrofuran having a molecular weight of 650, 1575 grams of 4-aminobenzoic acid ethylester, and 0.45 grams of titaniumtetrabutylate was heated to 200° C. for 22 hours, while the ethanol released was removed by distillation. After cooling, the product was obtained in the form of a yellow, highly viscous oil.

b) Preparation of the Bismaleimide

A solution of 890 grams of an amino-terminated polyoxybutylene, prepared according to a), in 2000 ml of acetone, was added dropwise over a one hour period to a solution of 196 grams of maleic anhydride in 2000 ml of acetone maintained at 0° C. The mixture was stirred an additional two hours without cooling, following which 360 grams of acetic anhydride, 60.6 grams of triethylamine and 5.88 grams of manganese(II) acetate- tetrahydrate was added. After heating for two hours at 40° C. and one hour at 50° C., all of the acetone was distilled off in a vacuum. The solution was washed once with 3,000 ml of water, following which 2500 ml of dichloromethane was added. The resulting solution was then washed eight times, each time with 2,000 ml of neutral water. The organic phase was dried over sodium sulfate and the solvent removed in vacuuo. Obtained was 1,005 g (96 percent) of the Bismaleimide as a yellowish, highly viscous oil.

The embodiments of the invention in which an exclusive property or privilege is claimed are defined as follows:

1. Bismaleimides having the general formula

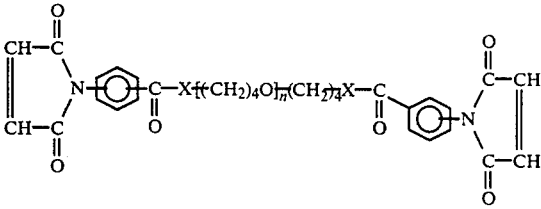

in which n is a whole number between 5 and 70 and each —X— may independently be —O— or —NH—.

2. The bismaleimide of claim 1 wherein —X— is —O—.

3. The bismaleimide of claim 1 wherein —X— is —NH—.

4. The bismaleimide of claim 2 wherein n is a whole number from about 7 to about 33.

5. The bismaleimide of claim 3 wherein n is a whole number from about 7 to about 33.

* * * * *

UNITED STATES PATENT AND TRADEMARK OFFICE
CERTIFICATE OF CORRECTION

PATENT NO. : 4,745,197
DATED : May 17, 1988
INVENTOR(S) : PHILIPP EISENBARTH ET AL

It is certified that error appears in the above-identified patent and that said Letters Patent is hereby corrected as shown below:

```
On first page of patent for bibliographic data under
ICI/REPAT CODE 30 Foreign Application Priority Data:
add July 2, 1986 (DE) Fed. Rep. of Germany - 3622088.
```

Signed and Sealed this

First Day of November, 1988

*Attest:*

DONALD J. QUIGG

*Attesting Officer*   *Commissioner of Patents and Trademarks*